United States Patent [19]

Kalvoda

[11] 4,221,786

[45] Sep. 9, 1980

[54] NOVEL HALOGENOPREGNADIENES AND PROCESS FOR THE MANUFACTURE THEREOF

[75] Inventor: Jaroslav Kalvoda, Binningen, Switzerland

[73] Assignee: Ciba-Geigy Corporation, Ardsley, N.Y.

[21] Appl. No.: 917,236

[22] Filed: Jun. 20, 1978

Related U.S. Application Data

[63] Continuation of Ser. No. 767,196, Feb. 9, 1977, abandoned.

[51] Int. Cl.$^2$ ............................................. A61K 31/58
[52] U.S. Cl. ........................ 424/241; 260/239.55 D; 260/397.45; 260/239.55 R
[58] Field of Search ............... 260/239.55 D; 424/241

[56] References Cited

U.S. PATENT DOCUMENTS

| | | | |
|---|---|---|---|
| 2,865,936 | 12/1958 | Schneider et al. | 260/239.55 D |
| 3,197,469 | 7/1965 | Fried et al. | 260/239.55 D |
| 3,678,034 | 7/1972 | Laurent et al. | 260/397.45 |
| 3,687,942 | 8/1972 | Anner | 260/239.55 D |
| 3,740,392 | 6/1973 | Heider et al. | 260/239.55 D |

FOREIGN PATENT DOCUMENTS

| | | | |
|---|---|---|---|
| 1921397 | 11/1970 | Fed. Rep. of Germany | 260/239.55 D |
| 2448548 | 11/1975 | Fed. Rep. of Germany | 260/239.55 D |
| 2291760 | 6/1976 | France | 260/239.55 D |

*Primary Examiner*—Elbert L. Roberts
*Attorney, Agent, or Firm*—Theodore O. Groeger

[57] ABSTRACT

The invention relates to the preparation of polyhalogenated pregnane derivatives of the formula

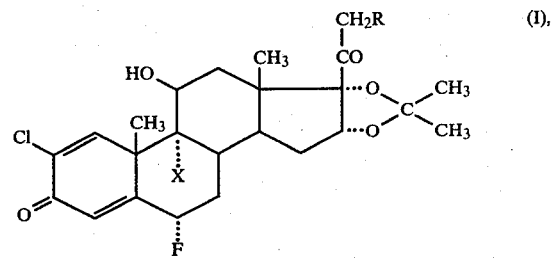

wherein X represents fluorine or chlorine and R a free or esterified hydroxyl group or chlorine. The new compounds display a high antiinflammatory activity. No side action on the thymus, the body weight or the adrenals can be detected at the therapeutic dose when the compounds are administered topically. The new compounds are therefore particularly suitable for use as medicaments in dermatology.

The new compounds can be prepared according to methods known in the art, e.g. by introducing the chlorine atom in 2-position of corresponding compounds which are non chlorinated in this position, or by the introduction of the halogen atom in 9-position starting from the 9,11β-epoxide or the 9,11-dehydro-compound or by acetonization of the 16,17-dihydroxy group or by replacing a 21-hydroxy group by chlorine.

6 Claims, No Drawings

NOVEL HALOGENOPREGNADIENES AND PROCESS FOR THE MANUFACTURE THEREOF

This is a continuation of application Ser. No. 767,196, filed on Feb. 9, 1977, now abandoned.

The invention provides polyhalogenated pregnane derivatives of the formula

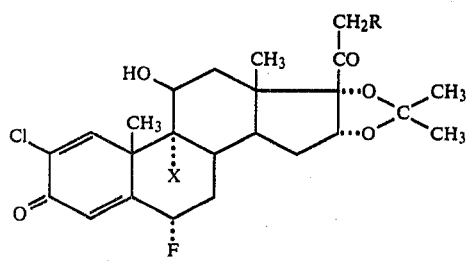

wherein X represents a fluorine or chlorine atom and R represents a free or esterified hydroxyl group or a chlorine atom, a process for the manufacture thereof, and pharmaceutical preparations which contain the novel compounds as active substances and the therapeutic use thereof.

An esterified hydroxyl group R is derived from acids which are customarily suitable as esterification compounds in hydroxysteroids intended for therapeutic use, for example from unsubstituted or substituted organic carboxylic acids containing 1 to 18 carbon atoms, from sulphonic acids or from inorganic acids. Preferred carboxylic acids of the aliphatic series are in particular the lower aliphatic mono- or dicarboxylic acids containing 1 to 7 carbon atoms, for example acetic acid, propionic acid, the butyric acids, the valeric acids, the caproic acids, in particular trimethylacetic acid, n-caproic acid, dimethylethylacetic acid, malonic acid, succinic acid, glutaric acid. Suitable higher aliphatic carboxylic acids are, for example, capric or undecylenic acid, palmitic acid, oleic acid or stearic acid. Examples of cycloaliphatic or cycloaliphatic-aliphatic monocarboxylic acids are cyclopropane-, cyclobutane-, cyclopentane- and cyclohexanecarboxylic acid and cyclopropyl- or cyclobutylmethanecarboxylic acid, or one of the cyclopentyl- or cyclohexylethanecarboxylic acids. Preferred substituted carboxylic acids are in particular the hydroxylated carboxylic acids, for example the malic acids, the lactic acids, the citric acids, glycolic or diglycolic acid, or alkoxycarboxylic acids, in particular lower alkoxycarboxylic acids, such as methoxy- or ethoxyacetic acid or methoxy- or ethoxypropionic acid. Aromatic carboxylic acids which are particularly suitable as esterification components are the monocyclic acids, such as benzoic acid and the derivatives thereof, or phthalic acid, and araliphatic carboxylic acids are monocyclic-lower aliphatic carboxylic acids, such as phenylacetic or phenylpropionic acid. The esterified hydroxyl groups can also however be derived from heterocyclic acids, for example from nicotinic or isonicotinic acid. Suitable sulphonic acids are chiefly methanesulphonic acid or monocyclic aromatic sulphonic acids, for example benzene- or toluenesulphonic acids, especially p-toluenesulphonic acid. Finally, the esterified group can be derived from inorganic acids, in particular sulphuric acid and ortho-, meta- or pyrophosphoric acid. The esters of polybasic acids are generally in the form of monoesters.

Water-soluble preparations of formula (I) can be obtained by advantageously preparing hemiesters of polybasic acids, such as dicarboxylic acids, for example succinic or phthalic acid, or of sulphuric acids or of phosphoric acids, and then converting these into salts of organic bases, for example of simple aliphatic amines, such as trimethylamine, diethylamine, ethylamine, propylamine or isopropylamine, or of cyclic bases, such as piperidine, morpholine or pyrrolidine, or the homologues thereof. However, for the same purpose it is also possible to prepare esters which are derived from a carboxylic acid which contains amino groups, for example diethylamino-, piperidino- or morpholinoacetic acid, or any other known amino acid, and to quaternise the amino group in these esters, so that the water-soluble quaternary ammonium salts are formed.

The novel compounds of the formula (I) possess valuable pharmacological properties. Thus they have a pronounced antiinflammatory action, as can be demonstrated in animal tests, for example on rats in the foreign body granuloma test. When applied locally in the dosage range between 0.003 mg per cotton wool pellet and 0.01 mg per cotton wool pellet they exhibit a marked antiinflammatory action. An action on the thymus, the adrenals and the body weight is observed in this mode of administration only from doses of 0.03 mg per cotton wool pellet. The above compounds of the formula (I), in which R represents a free hydroxyl group, and the lower aliphatic esters thereof, such as the acetates, propionates, butyrates, valerates, the hemi-succinates and also the phosphates, are particularly active.

The compounds of the above formula (I) can be obtained in a manner known per se. In particular they can be prepared by (a) introducing a 2-chlorine atom into a compound of the formula (I) in which this substituent is not present in the 2-position, or (b) treating a compound of the formula

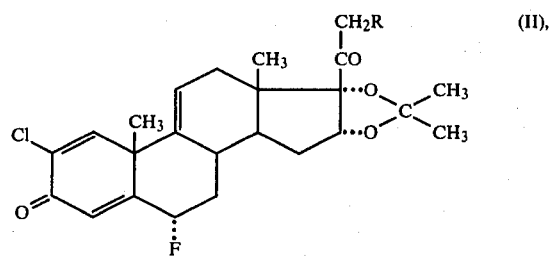

wherein R is as defined in formula (I), with hypochlorous acid or with a hypochlorous acid donor, or (c) treating a compound of the general formula

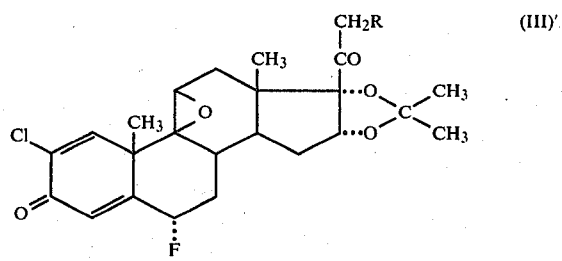

wherein R is as defined in formula (I), with hydrogen chloride or hydrogen fluoride or with agents which yield these hydrohalic acids, or (d) reacting a compound of the formula

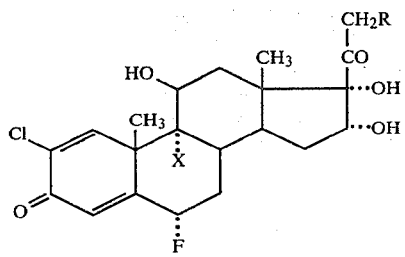

wherein R and X are as defined in formula (I), or a 16-ester thereof, with acetone or a functional derivative thereof, or (e) replacing the sulphonyloxy group OY by a chlorine atom in a compound of the formula

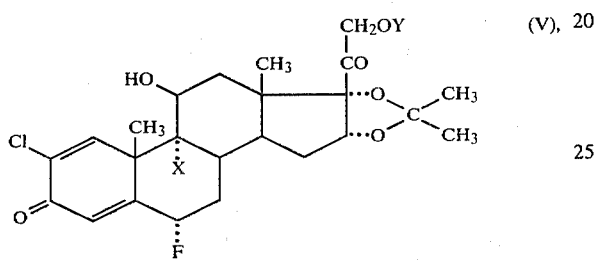

wherein X is as defined in formula (I) and Y represents the acyl radical of an organic sulphonic acid, and, if desired, in resultant compounds with an esterified hydroxyl group R in the 21-position, converting this group in a manner known per se into a free hydroxyl group, and/or esterifying a free hydroxyl group R in a manner known per se, and/or, if desired, converting hemiesters of dicarboxylic acids or of polybasic inorganic acids into their metal salts or salts of organic bases.

According to method (a), chlorine is added to the 1,2-double bond of the starting steroid in a manner known per se. To this end, preferably elementary chlorine is used and the chlorination is carried out in an inert solvent, for example an ether, such as dioxane or tetrahydrofurane, a halogenated hydrocarbon, for example methylene chloride, or a carboxylic acid, in particular a lower aliphatic carboxylic acid, such as acetic acid or propionic acid. Instead of using carboxylic acids it is also possible to use derivatives thereof, such as acid amides, for example dimethyl formamide, or nitriles, such as lower alkylnitriles, for example acetonitrile. Advantageously, mixtures of these solvents can also be used, in particular a mixture of an ether, such as dioxane, with one of the above mentioned lower aliphatic carboxylic acids. The process can be carried out with chlorine in an amount substantially in excess of the theoretical amount; but preferably the stoichiometric amount of chlorine is used. The chlorination is advantageously carried out at low temperature, approx. between −50° and +30° C., for example between −20° and +10° C., and in the dark. The reaction time is normally several hours or days, for example up to 7 days. In a particularly preferred embodiment of the process, the starting steroid is dissolved in one of the solvents mentioned above, for example dioxane, and treated with a solution of the chlorinating agent, for example chlorine, in a lower aliphatic carboxylic acid, for example propionic acid, and this solution is then allowed to stand at the given temperature for several days.

However, the chlorination of the 1,2-double bond can also be effected with mixtures of two different chlorine-containing compounds one of which yields positive and the other negative chlorine. Examples of suitable reagents which are able to set free positive chlorine are chlorinated acid amides or acid imides, such as chlorosuccinimide or chloroacetamide, and reagents which yield negative chlorine are, for example, hydrogen chloride and alkali metal chlorides. The above mentioned solvents can also be used for the addition of chlorine with these reagents.

If desired, the 11-hydroxyl group can be protected before the chlorination, preferably by esterification with trifluoroacetic acid. The trifluoroacetates are obtained by reacting the starting materials with trifluoroacetic chloride or anhydride in a manner known per se. It is known that this ester can be easily split off again by hydrolysis or solvolysis, for example by treatment with hydroxides, carbonates, bicarbonates or acetates of alkali metals or alkaline earth metals, for example in alcoholic or aqueous-alcoholic solution, for example in methanolic solution, or with alcohols alone. A particular method of carrying out the solvolysis of the 11-trifluoroacetate group is that described in German patent specification No. 1,593,519, which is chiefly suitable whenever it is a question of leaving the ester groups in 17- and/or 21-position intact. This method comprises treating the 11-ester in a lower alcohol with a salt of an acid whose pKa-value is in the range between about 2.3 and about 7.3, such as sodium or potassium azide or sodium or potassium formiate. If appropriate, this salt can also only be used in catalytic amounts. Furthermore, the hydrolysis of the 11-trifluoroacetate group can also be effected by treatment with other basic reagents, for example with amines, in particular heterocyclic bases, such as pyridine or collidine. Finally, the saponification by treatment with silica gel according to the process described in DT-OS 2,144,405 is also possible.

The 11-hydroxyl protective group can be removed immediately after the addition of chlorine to the 1,2-double bond or, if appropriate, simultaneously with dehydrochlorination by treatment with a base to be carried out, according to the process, after the chlorination. However, if desired, the protective group can be removed not until after the removal of hydrogen chloride by treatment with a base.

The dehydrochlorination of the 1,2-dichloro compounds obtained by the addition of chlorine in the 1,2-double bond can advantageously be accomplished with a base. Suitable bases are, for example, tertiary organic nitrogen bases, such as the lower aliphatic amines, for example triethylamine, or heterocyclic bases, such as pyridine and homologues thereof, for example collidine, or aromatic bases, such as N,N-dialkylaniline. However, it is also possible to use inorganic bases, such as in particular the alkali metal and alkaline earth metal salts also used for removing the above mentioned 11β-hydroxyl protective group, for example potassium or sodium acetate or potassium or sodium bicarbonate, in aqueous-alcoholic solution, and the corresponding hydroxides. The dehydrohalogenation is preferably carried out in the temperature range between approx. 20° and 100° C. and over the course of half an hour up to approx. 30 hours, depending on whether the reaction is carried out at elevated or low temperature. Preferably, an excess of the dehydrohalogenating agent is used.

According to method (b), the elements of hypochlorous acid are added in a manner known per se to the 9,11-double bond of the compounds of the formula (III) by, for example, treatment with aqueous hypochlorous acid or with hypochlorous acid donors, such as N-chlorocarboxamides or N-chlorocarboximides (cf. U.S. Pat. No. 3,057,886), in the presence of water and/or an inert solvent, such as a tertiary alcohol, for example butanol, an ether, for example diethyl ether, methyl isopropyl ether, dioxane, or a ketone, such as acetone, optionally in the presence of a strong acid. An advantageous method of carrying out this process is the reaction with tert.-butylhypochlorite in an inert water-immiscible solvent, for example a nitro-substituted hydrocarbon, in the presence of perchloric acid (cf. German patent specification No. 2,011,559). According to method (c), the $9\beta,11\beta$-oxido steroids of the indicated formula are treated in a manner known per se with hydrogen chloride or hydrogen fluoride, or with those agents which are capable of adding these hydrohalic acids to the epoxide to form the corresponding halohydrines. The process can be carried out in aqueous medium or in an inert organic solvent, such as an alcohol or an ether, in particular tetrahydrofurane or dioxane, and also for example diethyl ether or isopropyl ether, a hydrocarbon, such as methylene chloride or chloroform, or an acid amide, such as dimethyl formamide. As compounds which yield hydrogen chloride or hydrogen fluoride it is possible to use the salts of these acids with a tertiary organic base, for example pyridine. A particularly advantageous process is described and claimed in U.S. Pat. No. 3,211,758, in accordance with which the starting product is reacted with an adduct of hydrogen fluoride and urea.

According to method (d), a compound of the indicated formula or a 16-ester thereof is reacted with acetone in a manner known per se. The reaction with acetone is effected preferably in the presence of an acid catalyst. As strong acid catalysts there are used strong mineral acids, such as hydrochloric acid, sulphuric acids, phosphoric acids and especially perchloric acid, or organic sulphonic acids, such as camphorsulphonic acid, or in particular monocyclic aromatic sulphonic acids, such as p-toluenesulphonic acid or sulphosalicylic acid. Preferably an excess of acetone is used, so that it can also be used as solvent. However, the reaction with acetone can also be carried out in another organic solvent, for example a halogenated aliphatic hydrocarbon, such as chloroform or methylene chloride, or an amide, such as dimethyl formamide, or in a cyclic ether, such as tetrahydrofurane or dioxane. The 16,17-diols used as starting materials can also be formed in situ, for example by using a 16-ester of these diols and reacting it in their stead in the indicated manner with acetone when the free diols are formed as intermediates. Instead of acetone, it is also possible to use a reactive derivative, for example a ketal, such as one derived from a lower aliphatic alcohol, or an enol acylate, for example enol acetate.

The replacement of the sulphonyloxy group OY by chlorine in accordance with process (e) is also effected in a manner known per se. The organic sulphonic acid from which the acyl radical Y is derived, is an aliphatic or carbocyclic, optionally unsaturated or aromatic sulphonic acid, such as a substituted or unsubstituted, for example halogenated, lower alkanesulphonic acid, a cycloalkanesulphonic acid or camphorsulphonic acid, or a benzenesulphonic acid which is unsubstituted or substituted for example by lower alkyl, lower alkoxy, halogen and/or nitro. Trifluoromethanesulphonic acid, (+)-camphor-10-sulphonic acid-($\beta$), p-bromobenzenesulphonic acid and, and in particular, p-toluenesulphonic acid, and above all, methanesulphonic acid, may be mentioned as typical examples of such acids. The exchange reaction is normally carried out in such a manner that the corresponding above characterised 21-sulphonic acid ester is treated at elevated temperature with an alkali metal chloride in the presence of an aprotic organic solvent whose dielectric constant is in the region of 29 and higher. Chiefly an alkali metal chloride, in particular lithium chloride, is used. A suitable aprotic organic solvent whose dielectric constant is in the region of 29 or higher is in particular a dialkylsulphoxide, such as dimethyl sulphoxide, a N,N-dialkylamide of a lower aliphatic carboxylic acid, such as N,N'-dimethyl formamide and N,N'-dimethyl acetamide, an alkane-nitrile and alk-2-ene-nitrile, such as acetonitrile or propene nitrile, and hexaalkylphosphoric amide, such as hexamethylphosphoric amide. Preferably the process is carried out in the presence of at least one molar equivalent of this solvent, the preferred solvent being N,N-dimethyl formamide. The reaction is advantageously carried out between 100° C. and the boiling temperature of the reaction mixture using at least one molar equivalent of the alkali metal halide. The reaction mixture can also be diluted with a further solvent. To this end an organic ketone is advantageously used, in particular one belonging to the aliphatic or carbocyclic series having 3 to 10 carbon atoms, for example acetone, 2-butanone, 2-hexanone, cyclopentanone or cyclohexanone.

According to the process, an esterified hydroxyl group in the 21-position can, if desired, be converted into a free hydroxyl group. This conversion can be accomplished in a manner known per se, for example preferably by alkaline saponification with the hydroxides, carbonates or bicarbonates of alkali metals, in particular of sodium or potassium, for example in aqueous or aqueous-alcoholic solution. The use of an aqueous solution of sodium bicarbonate in methanol is preferred.

According to the process, however, it is also possible, if desired, to esterify a free 21-hydroxyl group. This esterification is again carried out in a manner known per se, for example by treating the steroid alcohol with a reactive derivative of the acid in question, for example an organic acid, in particular a carboxylic acid. In particular, the chlorides or the anhydrides of these acids are used, preferably in the presence of a tertiary base, such as pyridine or collidine.

If desired, 21-hemiesters of dicarboxylic acids, for example those mentioned above, can be converted in a manner known per into their salts, in particular the alkali salts. To this end they are treated for example with the hydroxides, carbonates or bicarbonates of alkali metals, especially of sodium or potassium, or with the desired organic base, for example in aqueous or aqueous-alcoholic solution.

The starting materials necessary for carrying out the above process methods are known or they can be prepared in a manner known per se. Thus, for example, compounds of the formula (V) can be prepared in such a way that starting compounds for the above processes (a) to (d), in which R represents a free hydroxyl group or a hydroxyl group which is esterified with a carboxylic acid, is reacted firstly according to one of these processes and subsequently, if necessary after liberation of the 21-hydroxyl group, this latter is esterified in a manner known per se with a sulphonic acid.

The invention also relates to those embodiments of the process in which a compound obtainable in any stage of the process is used as starting material and the missing steps are carried out, or the process is interrupted at any stage, or in which a starting material is formed under the reaction conditions.

The present invention also provides pharmaceutical preparations which contain as active ingredient a compound according to the invention of the formula (I) or a salt of such a compound with salt-forming properties, and a process for the manufacture of such pharmaceutical preparations.

Suitable pharmaceutical preparations are primarily ones for topical application, such as creams, ointments, pastes, foams, tinctures and solutions, which contain approx. 0.02% to approx. 0.1% of active compound, and also preparations for oral administration, for example tablets, coated tablets and capsules, and those for parenteral administration.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes for example isopropyl myristate, wool wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens); polyoxyethylene fatty alcohol ethers or esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the water phase include agents which reduce water loss through evaporation, for example polyalcohols, such as glycerol, sorbitol, propylene glycol and/or polyethylene glycols, as well as preservatives, perfumes etc.

Ointments are water-in-oil emulsions which contain up to 70%, preferably however approx. 20% to about 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerol, propylene glycol, sorbitol and/or polyethylene glycol, and preservatives, perfumes etc.

Greasy ointments are anhydrous and contain as base in particular hydrocarbons, for example paraffin, petroleum jelly and/or liquid paraffins, furthermore natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-absorption mentioned in connection with the ointments.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons, such as chlorofluoro-lower alkanes, for example dichlorodifluoromethane and dichlorotetrafluoroethane being used as propellants. For the oleaginous phase there are used, inter alia, hydrocarbons, for example paraffin oil, fatty alcohols, for example cetyl alcohol, fatty acid esters, for example isopropyl myristate; and/or other waxes. As emulsifiers there are used, inter alia, mixtures of those emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Tinctures and solutions generally have an aqueous ethanolic base to which are added, inter alia, polyalcohols, for example glycerol, glycols, and/or polyethylene glycol, as humectants for reducing water loss, and fat-restoring substances, such as fatty acid esters with lower polyethylene glycols, i.e. lipophilic substances which are soluble in the aqueous mixture as substitute for fatty substances which are taken from the skin with the ethanol, and, if necessary, other assistants and additives.

The pharmaceutical preparations for topical application are obtained in known manner, for example by dissolving or suspending the active substance in the base or in a part thereof, if necessary. When processing the active substance in the form of a solution, it is usually dissolved in one of the two phases before the emulsification, and when processing the active substance in the form of a suspension, it is mixed with a part of the base before the emulsification and then added to the remainder of the formulation.

Besides the pharmaceutical preparations which can be applied topically, other suitable preparations are those for enteral, for example oral, and parenteral administration to warm-blooded animals and which contain the pharmacologically active substance as sole ingredient or together with a pharmaceutically acceptable carrier. These pharmaceutical preparations contain about 0.01% to about 10% of active substance and are in dosage unit form, such as coated tablets, tablets, capsules, suppositories or ampoules. They are obtained in known manner, for examle by conventional mixing, granulating, coating, dissolving or lyophilising methods.

The dosage of active substance depends on the species of warm-blooded animal, the age, and the individual condition as well as on the mode of application.

The present invention also relates to the use of the novel compounds of the formula I and of the salts of such compounds with salt-forming properties, preferably for treating inflammations, chiefly as antiinflammatory glucocorticoids for local application, normally in the form of pharmaceutical preparations, especially in the form of pharmaceutical preparations for topical application.

The compounds of the present invention can also be used as additives to animal feeds.

The following Examples describe the invention in more detail.

EXAMPLE 1

A solution of 2.2 g of 6α,9α-difluoro-11β,21-dihydroxy-16α,17-isopropylidenedioxy-pregna-1,4-diene-3,20-dione-21-acetate in 175 ml of dioxane and 10.5 ml of an ice-cold solution prepared by introducing 7.70 g of chlorine into 100 ml of propionic acid are mixed, with cooling, and allowed to stand for 72 hours at 3° to 4° C. The reaction mixture is thereafter diluted with chloroform and washed in succession with potassium iodide/sodium thiosulphate solution, 1 N sodium hydroxide solution and with water. The aqueous solutions are extracted with chloroform and the combined organic phases are dried and the corresponding 1,2-dichloro compound is concentrated at approx. 40° C. in a water jet vacuum. The amorphous residue (2.9 g) is then dissolved in 60 ml of pyridine and the solution is allowed to stand for 18 hours at room temperature in the dark. The solution is then poured onto ice-water and stirred for 30 minutes. The precipitated substance is collected with suction, washed well with water and dissolved in chloroform. The solution is dried over sodium sulphate and concentrated in vacuo to yield 2.52 g of a yellowish amorphous product which is chromatographed through a column of 70 times its weight of silica gel with a mixture of toluene/ethyl acetate (90:10) as eluant. Recrystallisation of the pure fractions (2.2 g) from methylene chloride/methanol/ether yields the pure 2-chloro-6α,9α-difluoro-11β,21-dihydroxy-16α,17-isopropylidenedioxypregna-1,4-diene-3,20-dione-21-acetate which melts at 177°–179° C.

$[\alpha]_D^{25} = +58°$ (c=0.810; chloroform).

EXAMPLE 2

A solution of 1.45 g of 2-chloro-6α,9α-difluoro11β,21-dihydroxy-16α,17-isopropylidenedioxy-pregna-1,4-diene-3,20-dione-21-acetate in 100 ml of methanol and 8 ml of a 1 N sodium hydrogen carbonate solution are stirred under nitrogen for 3 hours at room temperature. Then 0.15 ml of glacial acetic acid and 75 ml of water are added and the solvent is evaporated at approx. 30° C. in vacuo. A further 70 ml of water are added and the reaction mixture is allowed to stand for 30 minutes at room temperature. The precipitate which has formed is collected with suction, washed with water and taken up in chloroform which contains methanol. The solution is dried and concentrated by rotary evaporation. The crude product (1.3 g) is dissolved in methylene chloride and filtered through a column of 30 g of silica gel using 300 ml of a 50:50 mixture of toluene/ethyl acetate as eluant. The solvent is evaporated to give 1.23 g of 2-chloro-6α,9α-difluoro-11β,21-dihydroxy-16α,17-isopropylidenedioxy-pregna-1,4-diene-3,20-dione. The compound which is recrystallised from methylene chloride/methanol/ether melts at 297°–301° C. (decomp.). $[\alpha]_D^{25} = +61°$ (c=0.509; dioxane).

EXAMPLE 3

A solution cooled to 0° C. of 1 g of 2-chloro-6α,9α-difluoro-11β,21-dihydroxy-16α,17-isopropylidenedioxy-pregna-1,4-diene-3,20-dione in 5 ml of pyridine is treated with 2 ml of valeric anhydride and the reaction mixture is allowed to stand for 3 hours at 3° to 4° C. With stirring, the reaction mixture is then poured onto ice/water and extracted twice with methylene chloride. The organic solutions are washed in succession with 2 N hydrochloric acid, dilute ice-cold sodium carbonate solution and repeatedly with water, dried and concentrated by rotary evaporation. The crude product is dissolved in methylene chloride, filtered through 30 g of alumina (activity II) and recrystallised from methylene chloride/ether/petroleum ether to yield the pure 2-chloro-6α,9α-difluoro-11β,21-dihydroxy-16α,17-isopropylidenedioxy-pregna-1,4-diene-3,20-dione-21-valerate with a melting point of 232°–233° C. (slight sintering at 130°–132° C.).

EXAMPLE 4

With stirring, a solution of 1.5 g of 2-chloro-6α,9α-difluoro-11β,21-dihydroxy-16α,17-isopropylidenedioxy-pregna-1,4-diene-3,20-dione in 30 ml of pyridine is treated dropwise at approx. −10° C. with 1.1 ml of methanesulphonyl chloride and the reaction mixture is allowed to stand for 20 hours at room temperature. The reaction mixture is subsequently poured onto 700 ml of ice/water and stirred for 20 minutes. The precipitate which has formed is collected with suction, washed with water, and taken up in methylene chloride. The solution is dried and concentrated in a water jet vacuum. The 21-mesylate obtained is dissolved direct in 50 ml of dimethyl formamide without further purification, and, after addition of 5.5 g of lithium chloride, the mixture is stirred under nitrogen for 3 hours at 100° C., cooled, and poured onto approx. 500 ml of ice/water. The precipitated product is collected with suction, washed with water and dissolved in methylene chloride. The solution is washed with water, dried and concentrated in vacuo. The residue is chromatographed through silica gel and subsequently crystallised from methylene chloride/methanol/ether to yield the pure 2,21-dichloro-6α,9α-difluoro-11β-hydroxy-16α,17α-isopropylidenedioxy-pregna-1,4-diene-3,20-dione with a melting point of 252°–254° C.

I claim:

1. A method of treating topical inflammations in warm-blooded animals, which comprises the topical administration of an antiinflammatory effective amount of a pharmaceutical preparation containing a polyhalogenated pregnane derivative of the formula

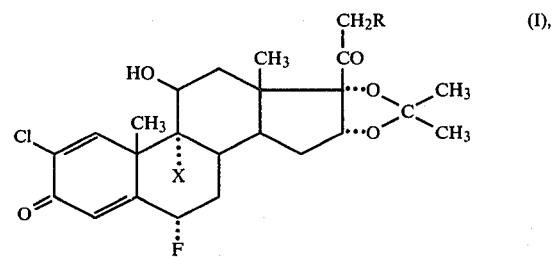

wherein X represents a fluorine or chlorine atom and R represents a hydroxyl group, a chlorine atom or a hydroxyl group esterified with an acid suitable for esterification of hydroxy-steroids useful in antiinflammatory therapy, together with a topically acceptable pharmaceutical carrier.

2. A method according to claim 1, in which said esterified hydroxyl groups R are derived from carboxylic acids containing 1 to 18 carbon atoms.

3. A method according to claim 1, in which said esterified hydroxyl groups R are derived from lower aliphatic carboxylic acids containing 1 to 7 carbon atoms.

4. A method according to claim 1, wherein said pregnane derivative is 2-chloro-6α,9α-difluoro-11β,21-dihydroxy-16α,17α-isopropylidene-dioxypregna-1,4-diene-3,20-dione.

5. A method according to claim 1, wherein said pregnane derivative is the 21-acetate of 2-chloro-6α,9α-difluoro-11β,21-dihydroxy-16α,17α-isopropylidene-dioxypregna-1,4-diene-3,20-dione.

6. A method according to claim 1, wherein said pregnane derivative is the 21-valerate of 2-chloro-6α,9α-difluoro-11β,21dihydroxy-16α,17α-isopropylidene-dioxypregna-1,4-diene-3,20-dione.

* * * * *